United States Patent
Hsu et al.

(10) Patent No.: US 10,813,627 B2
(45) Date of Patent: Oct. 27, 2020

(54) ULTRASOUND SYSTEM AND NOISE ELIMINATING METHOD

(71) Applicant: QISDA CORPORATION, Taoyuan (TW)

(72) Inventors: Chih-Hsiang Hsu, Tainan (TW); Chun-Chih Wang, Hsinchu County (TW); Chia-En Chuang, Hsinchu County (TW)

(73) Assignee: Qisda Corporation, Taoyuan (TW)

( * ) Notice: Subject to any disclaimer, the term of this patent is extended or adjusted under 35 U.S.C. 154(b) by 364 days.

(21) Appl. No.: 15/798,414

(22) Filed: Oct. 31, 2017

(65) Prior Publication Data

US 2018/0235579 A1  Aug. 23, 2018

(30) Foreign Application Priority Data

Feb. 21, 2017  (TW) .............................. 106105797 A

(51) Int. Cl.
 *A61B 8/00* (2006.01)
 *A61B 8/08* (2006.01)

(52) U.S. Cl.
 CPC .......... *A61B 8/5269* (2013.01); *A61B 8/5207* (2013.01); *A61B 8/54* (2013.01); *A61B 8/56* (2013.01)

(58) Field of Classification Search
 CPC ............................. A61B 8/5269; A61B 8/5207
 See application file for complete search history.

(56) References Cited

U.S. PATENT DOCUMENTS

2017/0065260 A1\* 3/2017 Arai .......................... A61B 8/56

FOREIGN PATENT DOCUMENTS

| CN | 1601299 A | 3/2005 |
|---|---|---|
| CN | 104287777 A | 1/2015 |
| CN | 104739446 A | 7/2015 |
| CN | 105806473 A | 7/2016 |
| JP | 4657044 B2 | 3/2011 |
| JP | 2014-83155 A | 5/2014 |
| TW | I492101 | 7/2015 |

\* cited by examiner

*Primary Examiner* — Joseph M Santos Rodriguez

(57) ABSTRACT

An ultrasound system includes an ultrasound probe, N switch elements and a processing unit, wherein the N switch elements are electrically connected to the ultrasound probe, the processing unit is electrically connected to the ultrasound probe and the N switch elements, and N is a positive integer. The ultrasound probe transmits and receives an ultrasound signal by a scanning frequency. Each of the switch elements has a main output frequency. The processing unit converts the ultrasound signal into an ultrasound image. The processing unit determines whether a noise exists in the ultrasound image. When the processing unit determines that the noise exists in the ultrasound image, the processing unit adjusts the main output frequency of at least one of the N switch elements.

10 Claims, 3 Drawing Sheets

ULTRASOUND SYSTEM AND NOISE ELIMINATING METHOD

BACKGROUND OF THE INVENTION

1. Field of the Invention

The invention relates to an ultrasound system and a noise eliminating method and, more particularly, to an ultrasound system and a noise eliminating method capable of eliminating a noise from an ultrasound image.

2. Description of the Prior Art

Since ultrasound scanning equipment does not destroy material structure and cell, the ultrasound scanning equipment is in widespread use for the field of material and clinical diagnosis. To enhance power efficiency, an ultrasound system is usually equipped with a lot of switch elements and different switch elements have different main output frequencies. The main output frequency of the switch element may interfere with an ultrasound image easily to generate a noise in the ultrasound image. Consequently, the interpretation of the ultrasound image will be affected. To prevent the ultrasound system from generating an abnormal ultrasound image, how to prevent the main output frequency of the switch element from generating a noise in the ultrasound image has become a significant design issue.

SUMMARY OF THE INVENTION

An objective of the invention is to provide an ultrasound system and a noise eliminating method capable of eliminating a noise from an ultrasound image, so as to solve the aforesaid problems.

According to an embodiment of the invention, an ultrasound system comprises an ultrasound probe, N switch elements and a processing unit, wherein the N switch elements are electrically connected to the ultrasound probe, the processing unit is electrically connected to the ultrasound probe and the N switch elements, and N is a positive integer. The ultrasound probe transmits and receives an ultrasound signal by a scanning frequency. Each of the switch elements has a main output frequency. The processing unit converts the ultrasound signal into an ultrasound image. The processing unit determines whether a noise exists in the ultrasound image. When the processing unit determines that the noise exists in the ultrasound image, the processing unit adjusts the main output frequency of at least one of the N switch elements.

According to another embodiment of the invention, a noise eliminating method is adapted to an ultrasound system. The ultrasound system comprises an ultrasound probe, N switch elements and a processing unit, wherein the N switch elements are electrically connected to the ultrasound probe, the processing unit is electrically connected to the ultrasound probe and the N switch elements, and N is a positive integer. Each of the switch elements has a main output frequency. The noise eliminating method comprises steps of the ultrasound probe transmitting and receiving an ultrasound signal by a scanning frequency; the processing unit converting the ultrasound signal into an ultrasound image; the processing unit determining whether a noise exists in the ultrasound image; and the processing unit adjusting the main output frequency of at least one of the N switch elements when the processing unit determines that the noise exists in the ultrasound image.

As mentioned in the above, when a noise exists in the ultrasound image, the noise may be generated by the main output frequency of the switch element. Accordingly, when the noise exists in the ultrasound image, the invention adjusts the main output frequency of the switch element, so as to eliminate the noise from the ultrasound image. It should be noted that if the noise cannot be eliminated from the ultrasound image after adjusting the main output frequencies of all of the switch elements, it represents that the noise is not generated by the main output frequency of the switch element. At this time, the noise has to be eliminated from the ultrasound image by other manners. In other words, the invention is to eliminate the noise generated by the main output frequency of the switch element by means of adjusting the main output frequency of the switch element.

These and other objectives of the present invention will no doubt become obvious to those of ordinary skill in the art after reading the following detailed description of the preferred embodiment that is illustrated in the various figures and drawings.

DETAILED DESCRIPTION

Figure 1:
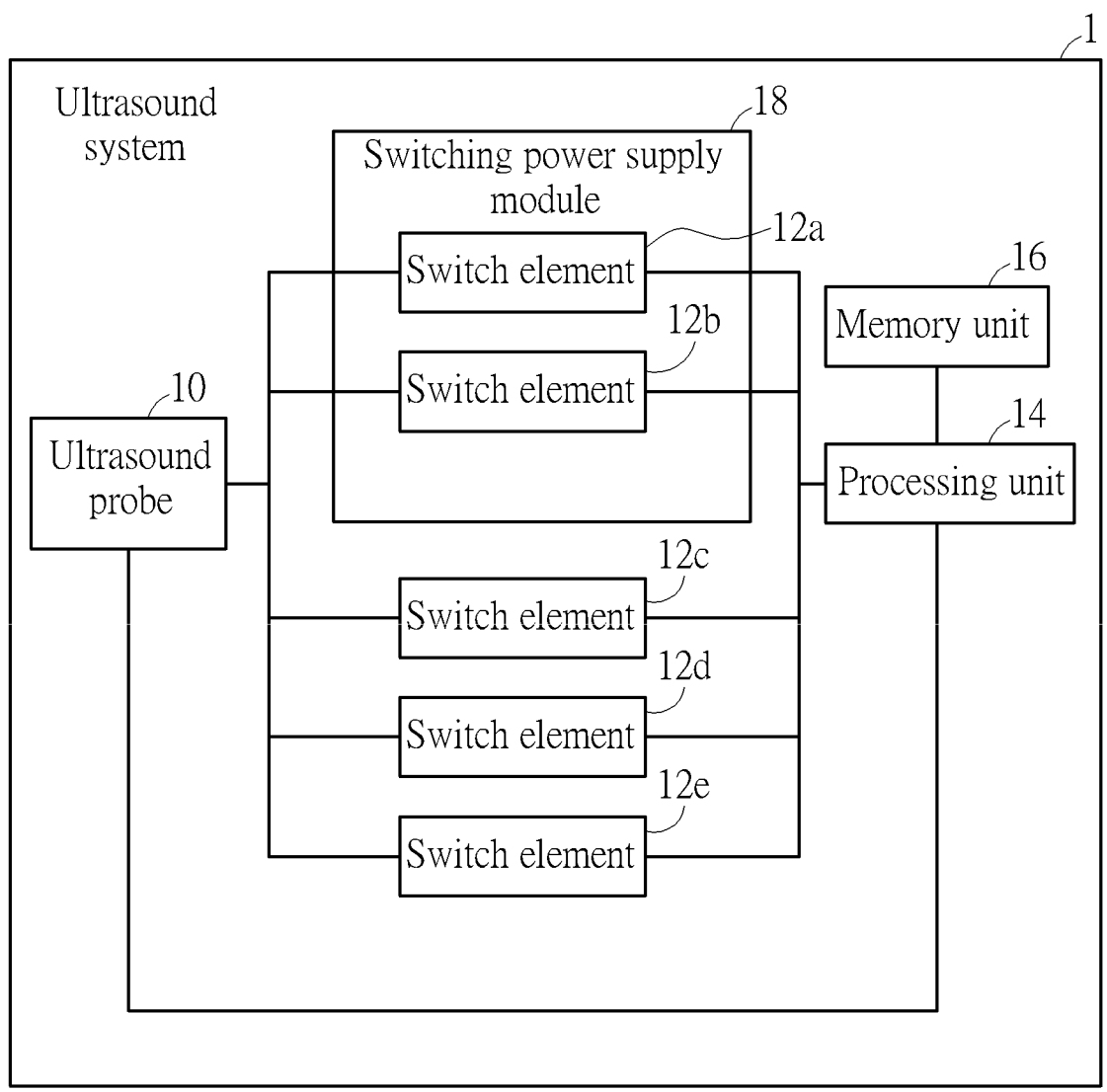
FIG. 1 is a functional block diagram illustrating an ultrasound system according to an embodiment of the invention.
Figure 2:
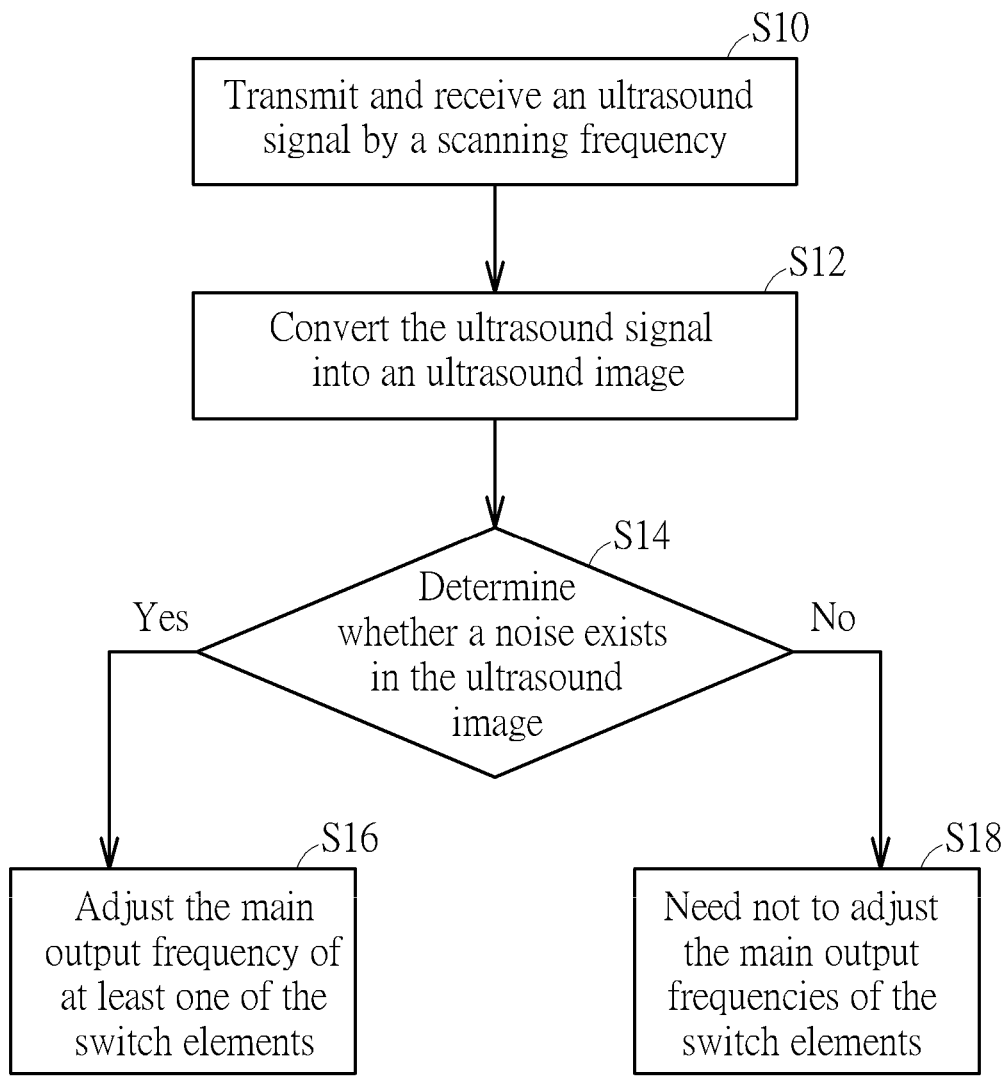
FIG. 2 is a flowchart illustrating a noise eliminating method according to an embodiment of the invention.

Referring to FIGS. 1 and 2, FIG. 1 is a functional block diagram illustrating an ultrasound system 1 according to an embodiment of the invention and FIG. 2 is a flowchart illustrating a noise eliminating method according to an embodiment of the invention. The noise eliminating method shown in FIG. 2 can be implemented by the ultrasound system 1 shown in FIG. 1.

As shown in FIG. 1, the ultrasound system 1 comprises an ultrasound probe 10, N switch elements 12a-12e, a processing unit 14 and a memory unit 16, wherein the N switch elements 12a-12e are electrically connected to the ultrasound probe 10, the processing unit 14 is electrically connected to the ultrasound probe 10, the N switch elements 12a-12e and the memory unit 16, and N is a positive integer. In this embodiment, N is equal to five. In other words, the ultrasound system 1 may comprise one or more switch elements according to practical applications. It should be noted that the ultrasound system 1 may be further equipped with other necessary circuits and components according to practical applications and those will not be depicted herein. Furthermore, the processing unit 14 may be a processor or a controller with signal processing function.

In this embodiment, the ultrasound system 1 may comprise a switching power supply module 18 electrically connected to the ultrasound probe 10 and the processing unit 14, wherein the switching power supply module 18 supplies a power for electronic components in the ultrasound system 1. At least one of the switch elements 12a-12e may be an electronic switch in the switching power supply module 18. As shown in FIG. 1, the switch elements 12a-12b are electronic switches in the switching power supply module 18. Still further, each of the switch elements 12a-12e has a main output frequency and the memory unit 16 stores the main output frequency of each of the switch elements 12a-12e.

To perform the noise eliminating method of the invention, first of all, the ultrasound probe 10 transmits and receives an ultrasound signal by a scanning frequency (step S10 in FIG. 2). Then, the processing unit 14 converts the ultrasound signal into an ultrasound image (step S12 in FIG. 2). Then, the processing unit 14 determines whether a noise exists in the ultrasound image (step S14 in FIG. 2). When the processing unit 14 determines that the noise exists in the ultrasound image, the processing unit 14 adjusts the main output frequency of at least one of the N switch elements 12a-12e (step S16 in FIG. 2). It should be noted that when the processing unit 14 determines that no noise exists in the ultrasound image, the processing unit 14 needs not to adjust the main output frequencies of the switch elements 12a-12e (step S18 in FIG. 2).

For further explanation, when a noise exists in the ultrasound image, the noise may be generated by the main output frequency of at least one of the switch elements 12a-12e. Accordingly, when the noise exists in the ultrasound image, the invention adjusts the main output frequency of at least one of the switch elements 12a-12e, so as to eliminate the noise from the ultrasound image. It should be noted that if the noise cannot be eliminated from the ultrasound image after adjusting the main output frequencies of all of the switch elements, it represents that the noise is not generated by the main output frequencies of the switch elements 12a-12e. At this time, the noise has to be eliminated from the ultrasound image by other manners. In other words, the invention is to eliminate the noise generated by the main output frequencies of the switch elements 12a-12e by means of adjusting the main output frequencies of the switch elements 12a-12e.

In this embodiment, the ultrasound probe 10 transmits and receives the ultrasound signal without aiming at an object. For example, the ultrasound probe 10 may transmit/receive the ultrasound signal to/from the air, such that the processing unit 14 converts the ultrasound signal into a blank ultrasound image. When the processing unit 14 analyzes that there is a solid line segment or a dashed line segment in the ultrasound image, the processing unit 14 may determine that the noise exists in the ultrasound image before the ultrasound probe 10 transmits/receives the ultrasound signal to/from an object.

In this embodiment, the processing unit 14 may convert the ultrasound signal into the ultrasound image by a pulse wave (PW) mode or a continuous wave (CW) mode. Furthermore, the scanning frequency of the ultrasound probe 10 may have an allowable range. In practical applications, the scanning frequency of the ultrasound probe 10 for transmitting the ultrasound signal may be slightly different from the scanning frequency of the ultrasound probe 10 for receiving the ultrasound signal. However, the scanning frequency of the ultrasound probe 10 for transmitting or receiving the ultrasound signal is still within the aforesaid allowable range. When the scanning frequency of the ultrasound probe 10 for transmitting the ultrasound signal is different from the scanning frequency of the ultrasound probe 10 for receiving the ultrasound signal, the scanning frequency mentioned in the invention represents the scanning frequency of the ultrasound probe 10 for receiving the ultrasound signal.

Figure 3:
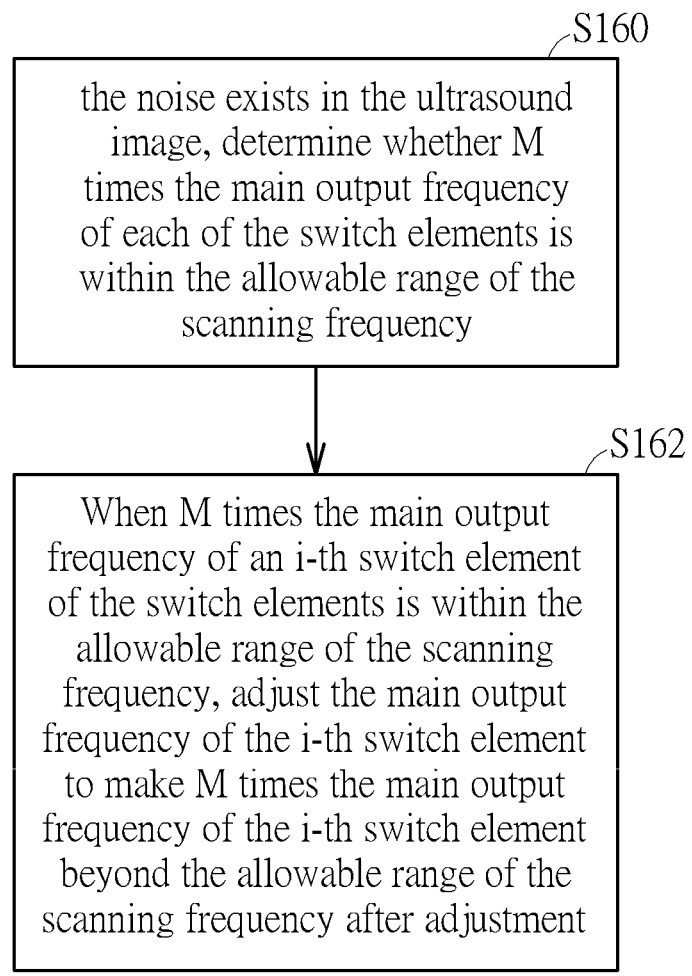
FIG. 3 is a flowchart illustrating the step S16 shown in FIG. 2 in detail according to an embodiment.

Referring to FIG. 3, FIG. 3 is a flowchart illustrating the step S16 shown in FIG. 2 in detail according to an embodiment. When the processing unit 14 determines that the noise exists in the ultrasound image, the processing unit 14 may further determine whether M times the main output frequency of each of the switch elements 12a-12e is within the allowable range of the scanning frequency (step S160 in FIG. 3). When the processing unit 14 determines that M times the main output frequency of an i-th switch element of the switch elements 12a-12e is within the allowable range of the scanning frequency, the processing unit 14 adjusts the main output frequency of the i-th switch element to make M times the main output frequency of the i-th switch element beyond the allowable range of the scanning frequency after adjustment (step S162 in FIG. 3). In this embodiment, M is a positive integer and i is a positive integer smaller than or equal to N. It should be noted that the processing unit 14 may increase or decrease the main output frequency of the i-th switch element according to practical applications as long as M times the main output frequency of the i-th switch element is beyond the allowable range of the scanning frequency after adjustment.

For example, provided that the scanning frequency of the ultrasound probe 10 is set to be 1400 KHz, the allowable range is set to be ±50 KHz, and the main output frequency of the switch element 12a is set to be 350 KHz. Since four times the main output frequency of the switch element 12a (i.e. 350 KHz*4=1400 KHz) is within the allowable range of the scanning frequency (i.e. 1400±50 KHz), the processing unit 14 may increase the main output frequency of the switch element 12a to be, for example, 400 KHz or decrease the main output frequency of the switch element 12a to be, for example, 300 KHz, so as to make M times the main output frequency of the switch element 12a beyond the allowable range of the scanning frequency after adjustment. Accordingly, the invention can prevent the main output frequency of the switch element 12a from generating a noise in the ultrasound image.

It should be noted that when M times the main output frequency of more than one switch element is within the allowable range of the scanning frequency, the processing unit 14 has to adjust the main output frequency of each switch element to make M times the main output frequency of each switch element beyond the allowable range of the scanning frequency after adjustment.

As mentioned in the above, when a noise exists in the ultrasound image, the noise may be generated by the main output frequency of the switch element. Accordingly, when the noise exists in the ultrasound image, the invention adjusts the main output frequency of the switch element, so as to eliminate the noise from the ultrasound image. It should be noted that if the noise cannot be eliminated from the ultrasound image after adjusting the main output frequencies of all of the switch elements, it represents that the noise is not generated by the main output frequency of the switch element. At this time, the noise has to be eliminated from the ultrasound image by other manners. In other words, the invention is to eliminate the noise generated by the main output frequency of the switch element by means of adjusting the main output frequency of the switch element.

Those skilled in the art will readily observe that numerous modifications and alterations of the device and method may be made while retaining the teachings of the invention. Accordingly, the above disclosure should be construed as limited only by the metes and bounds of the appended claims.

What is claimed is:
1. An ultrasound system comprising:
an ultrasound probe transmitting and receiving an ultrasound signal by a scanning frequency;

N switch elements electrically connected to the ultrasound probe, each of the switch elements having a main output frequency, N being a positive integer; and a processor electrically connected to the ultrasound probe and the N switch elements, the processor converting the ultrasound signal into an ultrasound image, the processor determining whether a noise exists in the ultrasound image, the processor adjusting the main output frequency of at least one of the N switch elements when the processor determines that the noise exists in the ultrasound image, the processor needing not to adjust the main output frequencies of the switch elements when the processor determines that no noise exists in the ultrasound image.

2. The ultrasound system of claim 1, wherein the ultrasound probe transmits and receives the ultrasound signal without aiming at an object and the processor determines that the noise exists in the ultrasound image when the processor analyzes that there is a solid line segment or a dashed line segment in the ultrasound image.

3. The ultrasound system of claim 1, further comprising a switching power supply module electrically connected to the ultrasound probe and the processor and supplying a power, wherein at least one of the N switch elements is an electronic switch in the switching power supply module.

4. The ultrasound system of claim 1, wherein the processor converts the ultrasound signal into the ultrasound image by a pulse wave mode or a continuous wave mode, the scanning frequency has an allowable range; when the processor determines that the noise exists in the ultrasound image, the processor determines whether M times the main output frequency of each of the switch elements is within the allowable range of the scanning frequency; when the processor determines that M times the main output frequency of an i-th switch element of the switch elements is within the allowable range of the scanning frequency, the processor adjusts the main output frequency of the i-th switch element to make M times the main output frequency of the i-th switch element beyond the allowable range of the scanning frequency after adjustment; M is a positive integer and i is a positive integer smaller than or equal to N.

5. The ultrasound system of claim 1, further comprising a memory unit electrically connected to the processor, the memory unit storing the main output frequency of each of the switch elements.

6. A noise eliminating method adapted to an ultrasound system, the ultrasound system comprising an ultrasound probe, N switch elements and a processor, the N switch elements being electrically connected to the ultrasound probe, the processor being electrically connected to the ultrasound probe and the N switch elements, each of the switch elements having a main output frequency, N being a positive integer, the noise eliminating method comprising steps of:

the ultrasound probe transmitting and receiving an ultrasound signal by a scanning frequency;

the processor converting the ultrasound signal into an ultrasound image;

the processor determining whether a noise exists in the ultrasound image;

the processor adjusting the main output frequency of at least one of the N switch elements when the processor determines that the noise exists in the ultrasound image; and the processor needing not to adjust the main output frequencies of the switch elements when the processor determines that no noise exists in the ultrasound image.

7. The noise eliminating method of claim 6, wherein the ultrasound probe transmits and receives the ultrasound signal without aiming at an object and the processor determines that the noise exists in the ultrasound image when the processor analyzes that there is a solid line segment or a dashed line segment in the ultrasound image.

8. The noise eliminating method of claim 6, wherein the ultrasound system further comprises a switching power supply module electrically connected to the ultrasound probe and the processor and supplying a power, and at least one of the N switch elements is an electronic switch in the switching power supply module.

9. The noise eliminating method of claim 6, wherein the processor converts the ultrasound signal into the ultrasound image by a pulse wave mode or a continuous wave mode, the scanning frequency has an allowable range, the noise eliminating method further comprises steps of:

when the processor determines that the noise exists in the ultrasound image, the processor determining whether M times the main output frequency of each of the switch elements is within the allowable range of the scanning frequency, wherein M is a positive integer; and when the processor determines that M times the main output frequency of an i-th switch element of the switch elements is within the allowable range of the scanning frequency, the processor adjusting the main output frequency of the i-th switch element to make M times the main output frequency of the i-th switch element beyond the allowable range of the scanning frequency after adjustment, wherein i is a positive integer smaller than or equal to N.

10. The noise eliminating method of claim 6, wherein the ultrasound system further comprises a memory unit electrically connected to the processor and the memory unit stores the main output frequency of each of the switch elements.

* * * * *